United States Patent
Ishida et al.

(10) Patent No.: US 9,981,089 B2
(45) Date of Patent: May 29, 2018

(54) GASKET FOR PRE-FILLED SYRINGE

(71) Applicant: SUMITOMO RUBBER INDUSTRIES, LTD., Kobe-shi, Hyogo (JP)

(72) Inventors: Naoyuki Ishida, Kobe (JP); Kazuhiro Fujisawa, Kobe (JP)

(73) Assignee: SUMITOMO RUBBER INDUSTRIES, LTD., Kobe-Shi, Hyogo (JP)

(*) Notice: Subject to any disclaimer, the term of this patent is extended or adjusted under 35 U.S.C. 154(b) by 190 days.

(21) Appl. No.: 15/021,365

(22) PCT Filed: Sep. 12, 2014

(86) PCT No.: PCT/JP2014/074265
§ 371 (c)(1),
(2) Date: Mar. 11, 2016

(87) PCT Pub. No.: WO2015/049972
PCT Pub. Date: Apr. 9, 2015

(65) Prior Publication Data
US 2016/0220758 A1    Aug. 4, 2016

(30) Foreign Application Priority Data
Oct. 2, 2013   (JP) ................. 2013-207511

(51) Int. Cl.
*A61M 5/31*    (2006.01)
*A61M 5/315*   (2006.01)

(52) U.S. Cl.
CPC ...... *A61M 5/31513* (2013.01); *A61M 5/3129* (2013.01); *A61M 2005/3101* (2013.01); *A61M 2005/3131* (2013.01)

(58) Field of Classification Search
CPC ............ A61M 5/31513; A61M 5/3129; A61M 2005/3131; A61M 2005/3101
See application file for complete search history.

(56) References Cited

U.S. PATENT DOCUMENTS 3,874,382 A * 4/1975 Nogier .............. A61M 5/31513
                                                604/222
6,511,459 B1 * 1/2003 Fago .................. A61M 5/31511
                                                604/122

(Continued)

FOREIGN PATENT DOCUMENTS

JP    2001-190667 A     7/2001
JP    2001190667 A *    7/2001    ........ A61M 5/31513

(Continued)

OTHER PUBLICATIONS

Machine translation of JP-2013-138697-A dated Jul. 18, 2013.

(Continued)

*Primary Examiner* — Thomas E Lazo
(74) *Attorney, Agent, or Firm* — Birch, Stewart, Kolasch & Birch, LLP

(57) ABSTRACT

The present invention provides a gasket for prefilled syringes having both airtightness and operability. The present invention relates to a gasket for prefilled syringes, the gasket including a plurality of circular ribs that are to be in sliding contact with the inner wall of a syringe, the gasket being laminated with an inert film, the plurality of circular ribs including a front circular rib having a front corner with a radius of curvature R1 and a rear corner with a radius of curvature R2, a ratio of the radius of curvature R2 to the radius of curvature R1 being more than 1.

14 Claims, 1 Drawing Sheet

(56) References Cited

U.S. PATENT DOCUMENTS

2005/0010175 A1 1/2005 Beedon et al.
2010/0042055 A1 2/2010 Sudo et al.

FOREIGN PATENT DOCUMENTS

| JP | 2002-86481 A | | 3/2002 | | |
|----|--------------|---|--------|---|---|
| JP | 2006-519070 A | | 8/2006 | | |
| JP | 2013-138697 A | | 7/2013 | | |
| JP | 2013138697 A | * | 7/2013 | ........ | A61M 5/31511 |
| WO | WO 2008/078467 A1 | | 7/2008 | | |
| WO | WO 2012147545 A1 | * | 11/2012 | ............ | A61M 5/315 |

OTHER PUBLICATIONS

International Search Report, issued in PCT/JP2014/074265, dated Dec. 9, 2014.
Written Opinion of the International Searching Authority, issued in PCT/JP2014/074265 (PCT/ISA/237), dated Dec. 9, 2014.

* cited by examiner

GASKET FOR PRE-FILLED SYRINGE

TECHNICAL FIELD

The present invention relates to a gasket for prefilled syringes, and specifically a gasket for prefilled syringes having a film laminated on a surface of the gasket.

BACKGROUND ART

Gaskets are required to have properties including airtightness and low sliding resistance. Airtightness refers to the ability to allow the liquid contents to be used without leaking outside and also prevent outside foreign substances from entering. Low sliding resistance refers to the ability to allow the operator of the prefilled syringe to move the gasket using the plunger with one hand without difficulty.

Higher airtightness between the gasket and the inner periphery of the barrel increases the sliding resistance of the gasket to the inner periphery, thereby deteriorating operability. For example, a method for solving this problem is known which improves the sliding properties of the outer surface of a gasket by laminating the outer surface with the low-friction material fluororesin (Patent Literature 1). However, when the gasket laminated with such a fluororesin film is inserted into a barrel, the maximum diameter portion (peak portion) of the gasket contracts due to a reaction force from the inner face of the barrel, thereby causing wrinkles or sagging in the fluororesin film on the portion. The wrinkles form gaps between the peak portion of the gasket and the inner face of the barrel, thereby reducing the airtightness of the gasket so that liquid leakage can be caused.

CITATION LIST

Patent Literature

Patent Literature 1: JP 2002-86481 A

SUMMARY OF INVENTION

Technical Problem

The present invention aims to provide a gasket for prefilled syringes having both airtightness and operability.

Solution to Problem

Gaskets have lower sliding resistance when the gaskets have a shorter contact portion with a barrel and when the gaskets have a smaller diameter so that they are less compressed upon being inserted into a barrel. On the other hand, the airtightness of gaskets is in a trade-off relationship with the sliding resistance. Gaskets having a shorter contact length with a barrel have lower airtightness. Further, gaskets having a smaller product diameter give a lower surface pressure to a barrel and thus have lower airtightness.

In this context, the present inventors have found that the shape of a portion connecting the peak portion and the valley portion and the shape of the peak portion are factors to increase the sliding resistance of the gasket. Then, the inventors have verified that the surface pressure of the gasket on the inner face of the barrel can be reduced by altering the shape of the gasket and accordingly completed the present invention.

The present invention relates to a gasket for prefilled syringes, the gasket including a plurality of circular ribs that are to be in sliding contact with an inner wall of a syringe, the gasket being laminated with an inert film, the plurality of circular ribs including a front circular rib having a front corner with a radius of curvature R1 and a rear corner with a radius of curvature R2, a ratio of the radius of curvature R2 to the radius of curvature R1 being more than 1.

Preferably, the ratio of R2 to R1 is 1.2 to 4.

Preferably, R1 is 0.3 to 1.0 mm and R2 is 0.5 to 3.5 mm.

Provided that a sliding portion of the gasket, including the corner, has a length H2, and a linear portion of the front circular rib has a length H1, a ratio of the length H2 to the length H1 is preferably 2 to 5.

Provided that a sliding portion of the gasket has a diameter H4, and a barrel of the syringe into which the gasket is to be inserted has an inner diameter H3, a ratio of the diameter H4 to the inner diameter H3 is preferably 1.01 to 1.10.

The inert film is preferably a fluororesin film, a nylon resin film, or an olefinic resin film.

Advantageous Effects of Invention

The gasket for prefilled syringes of the present invention includes a plurality of circular ribs that are to be in sliding contact with the inner wall of a syringe, and is laminated with an inert film. The plurality of circular ribs include a front circular rib having a front corner with a radius of curvature R1 and a rear corner with a radius of curvature R2, and the ratio of the radius of curvature R2 to the radius of curvature R1 is more than 1. Notwithstanding that such a gasket can be operated by an operator of the prefilled syringe with one hand without difficulty in medical practice, it is excellent in airtightness.

DESCRIPTION OF EMBODIMENTS

The gasket for prefilled syringes of the present invention has the following features: The gasket includes a plurality of circular ribs that are to be in sliding contact with the inner wall of a syringe, and is laminated with an inert film. The plurality of circular ribs include a front circular rib having a front corner with a radius of curvature R1 and a rear corner with a radius of curvature R2, and the ratio of the radius of curvature R2 to the radius of curvature R1 is more than 1.

Figure 1:
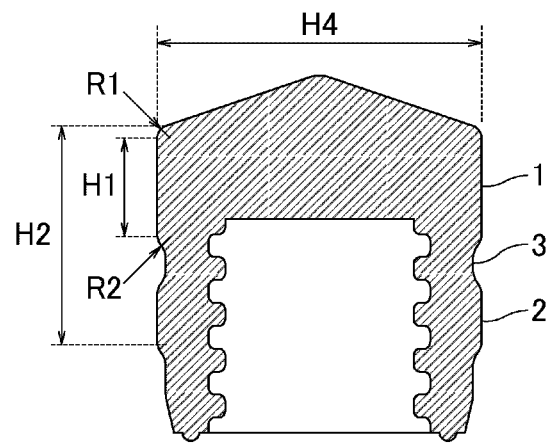
FIG. 1 shows a cross-sectional view of a gasket for prefilled syringes of the present invention.
Figure 2:
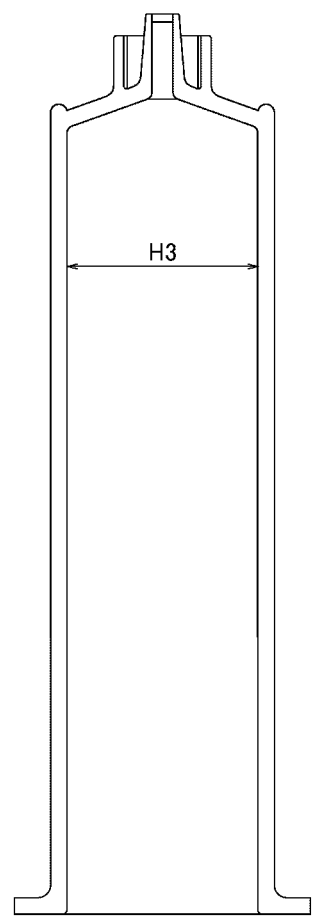
FIG. 2 shows a cross-sectional view of a syringe barrel portion of a prefilled syringe.

The gasket of the present invention includes a plurality of circular ribs that are to be in sliding contact with the inner wall of a syringe (barrel), and the circular ribs form a sliding portion. The term "a plurality of" refers to any number of two or more. For example, the gasket for prefilled syringes shown in FIG. 1 has two circular ribs including a front circular rib 1 and a rear circular rib 2. The portion designated by 3 is a valley portion which is not to be in sliding contact with the barrel.

Regarding the front circular rib among the circular ribs, the ratio of the radius of curvature R2 of the rear corner to the radius of curvature R1 of the front corner needs to be more than 1, preferably 1.2 to 4, more preferably 1.2 to 3.5. If the ratio is less than 1, sliding resistance increases. The front circular rib herein refers to a circular rib closest to the top surface of the gasket among the circular ribs.

R1 is preferably 0.3 to 1.0 mm, more preferably 0.3 to 0.8 mm. If R1 is less than 0.3 mm, the gasket tends to give an unnecessarily high contact pressure to the barrel, causing an increase in sliding resistance. If R1 is more than 1.0 mm, the sealing properties of the circular rib on the front side tend to decrease, thereby causing liquid leakage. Moreover, R1 depends on the size of syringe. R1 for a 1-mL syringe is preferably 0.3 to 0.5 mm.

R2 is preferably 0.5 to 3.5 mm, more preferably 0.6 to 3.0 mm. If R2 is less than 0.5 mm, the gasket tends to give an unnecessarily high contact pressure to the barrel, causing an increase in sliding resistance. If R2 is more than 3.5 mm while maintaining the contact area between the circular ribs and the barrel, the full length of the gasket tends to increase, thereby causing more molding defects. Moreover, R2 depends on the size of syringe. R2 for a 1-mL syringe is preferably 1.5 to 3.0 mm.

The ratio of the length H2 of the sliding portion of the gasket, including the front corner of the front circular rib to the length H1 of the linear portion of the front circular rib is preferably 2 to 5, more preferably 2 to 4. If the ratio is less than 2, the contact area between the circular ribs and the barrel tends to increase, thereby causing an increase in sliding resistance. If the ratio is more than 5, the contact area between the circular ribs and the barrel tends to decrease, thereby causing an increase in liquid leakage. The front circular rib has a substantially constant outer diameter in the H1 region.

The ratio of the diameter H4 of the sliding portion of the gasket to the inner diameter H3 of the barrel of the syringe into which the gasket is to be inserted is preferably 1.01 to 1.10, more preferably 1.01 to 1.05. If the ratio is less than 1.01, the contact pressure between the circular ribs and the barrel tends to decrease so that liquid leakage can occur easily. If the ratio is more than 1.10, the contact pressure between the circular ribs and the barrel tends to increase, resulting in increased sliding resistance.

The inert film is laminated not only on the liquid-contact portion (top surface) of the gasket but also the sliding portion of the gasket. The sliding portion is preferably laminated to cover at least a rear-side circular rib.

The inert resin film used for molding preferably has a thickness of 25 to 150 μm, more preferably 50 to 100 μm. A film having a thickness of less than 25 μm tends to be frequently torn upon molding, while a film having a thickness of more than 150 μm tends to result in economical disadvantages due to the dimension stability of the molded product and increased cost.

The inert film is not particularly limited but is preferably a fluororesin film, a nylon resin film, or an olefinic resin film. For good chemical resistance, examples of the fluororesin of the fluororesin film include polytetrafluoroethylene (PTFE), tetrafluoroethylene-ethylene copolymer (ETFE), perfluoroalkyl vinyl ether copolymer (PFA), tetrafluoroethylene-hexafluoropropylene copolymer (FEP), polychlorotetrafluoroethylene (PCTFE), polyvinylidene fluoride (PVDF), and polyvinyl fluoride (PVF). Moreover, although containers for medical use are sterilized by steam sterilization, ethylene oxide gas sterilization, or gamma-ray sterilization, PTFE is less resistant to gamma rays. Thus, ETFE, modified ETFE, and PCTFE, which are highly resistant to gamma-ray sterilization, are particularly preferred.

The ETFE refers to a copolymer of ethylene and tetrafluoroethylene at a molar ratio of 30/70 to 70/30, and it can further be copolymerized with other components for the purpose of modification to prepare modified ETFE. Examples of the other components include fluorine-containing olefins and hydrocarbon olefins. Specific examples include α-olefins such as propylene and butene; fluorine-containing olefins such as hexafluoropropylene, vinylidene fluoride, perfluorobutyl ethylene, and trifluorochloroethylene; vinyl ethers such as ethylene vinyl ether, perfluoromethyl vinyl ether, and perfluoropropyl vinyl ether; and fluorine-containing acrylates. These components in an amount of about 2 to 10 mol % are copolymerized to modify ETFE.

The modified ETFE may suitably be an ETFE containing an adhesion-imparting functional group. Examples of such a functional group include a carboxyl group, carboxylic anhydride group, epoxy group, hydroxy group, isocyanato group, ester group, amido group, aldehyde group, amino group, cyano group, carbon-carbon double bond, sulfonate group, and ether group. Moreover, examples of commercial products of the modified ETFE include Fluon AH-2000 (Asahi Glass Co., Ltd.).

Non-limiting examples of the nylon resin of the nylon resin film include nylon 6, nylon 11, nylon 12, nylon 66, nylon 610, nylon 6T, nylon 61, nylon 9T, and nylon M5T.

Examples of the olefin resin of the olefinic resin film include polyethylenic resins such as polyethylene, ethylene-propylene copolymer, ethylene-propylene-non-conjugated diene copolymer, ethylene-butene copolymer, ethylene-hexene copolymer, ethylene-octene copolymer, ethylene-vinyl acetate copolymer, ethylene-vinyl alcohol copolymer, ethylene-ethyl acrylate copolymer, and chlorinated polyethylene; polypropylenic resins such as polypropylene, propylene-ethylene random copolymer, propylene-ethylene block copolymer, and chlorinated polypropylene; and polybutene, polyisobutylene, polymethylpentene, and copolymers of cyclic olefins. Polyethylene, and especially ultra-high-molecular-weight polyethylene (UHMWPE), is preferred. These olefin resins may contain fluorine.

The inert film is preferably subjected to a treatment to enhance adhesion to rubber or the like. Examples of such a treatment to enhance adhesion include chemical treatments, treatments for roughing the surface of a film, and combinations thereof. Specific examples include sodium treatment, glow discharge treatment, plasma treatment (discharge treatment) under the atmospheric pressure or in vacuum, excimer laser treatment (discharge treatment), and ion beam treatment.

The base material of the gasket may be any elastic material. Examples include various rubber materials such as natural rubber, butyl rubber, polyisoprene rubber, polybutadiene rubber, styrene-butadiene rubber, silicone rubber, epichlorohydrin rubber, ethylene-propylene rubber, and nitrile rubber; and various thermoplastic elastomers such as polyurethane elastomers, polyester elastomers, polyamide elastomers, olefinic elastomers, and styrenic elastomers. These elastic materials may be used alone or as a blend of a plurality of materials. Among others, preferred are materials that acquire elasticity by vulcanization. In the case of vulcanizable materials, compounding ingredients known in the rubber industry, such as vulcanizing agents e.g. sulfur or vulcanization accelerators may be appropriately added.

The gasket of the present invention can be obtained as follows. The compounding materials are kneaded at a predetermined compounding ratio using an internal mixer, an open roll mill, or the like to prepare a kneaded mixture. This kneaded mixture is formed into an unvulcanized rubber sheet using a calender or sheet forming machine. Next, the unvulcanized rubber sheet with a predetermined weight and size and an inert film are stacked and placed on a mold and then molded using a vacuum press to give a molded laminated gasket sheet.

The molding conditions are not particularly limited and may be set appropriately. The molding temperature preferably ranges from 155° C. to 200° C., more preferably from 165° C. to 180° C. The molding time is preferably 1 to 20 minutes, more preferably 3 to 15 minutes, still more preferably 5 to 10 minutes.

Then, unnecessary portions are cut and removed from the molded gasket, and the resulting gasket is washed, sterilized, dried, and checked for its appearance to prepare a completed gasket. The gasket laminated with the inert film is inserted into a prefilled syringe barrel to prepare a prefilled syringe.

EXAMPLES

The present invention will be described in detail below with reference to, but not limited to, examples.

Examples 1-5 and Comparative Example 1

A PTFE film (trade name "New Valflon", Nippon Valqua Industries, Ltd., film thickness: 70 μm) was stacked on an unvulcanized rubber sheet formed from a chlorinated butyl rubber (ExxonMobil Chemical), and the stack was placed on a mold and molded at 175° C. for 10 minutes using a vacuum press for vulcanization bonding. The molded sheet was punched and washed to prepare a gasket (for 1-mL COP resin syringes with a barrel inner diameter of 6.3 mm). The sliding resistance and liquid leakage of the thus prepared gaskets were evaluated for n=20 as described below.

(Sliding Resistance)

The gaskets were measured using a desktop autograph available from Shimadzu Corporation with a stroke of 20 mm at a speed of 100 mm/min. As well as determining the sliding resistance, the sliding properties were evaluated based on the following criteria.

Good: The gasket slid without pulsations.
Poor: The gasket slid with pulsations.

(Liquid Leakage)

The experiment was performed in conformity with the Notification "Mekkin-zumi chusha-tou kijun (standards for sterile injection syringes)" issued on Dec. 11, 1998, Iyaku-hatsu No. 1079 by the Director of the Pharmaceutical and Medical Safety Bureau, the Ministry of Health, Labor and Welfare. A gasket sample for 1-mL syringes, a nozzle cap, a 1-mL syringe barrel, and a plunger were prepared. A jig was fit into the screw portion of the gasket. The jig was longer than the corresponding screw. The gasket in this state was placed with the liquid-contact face facing upward. Then, the gasket was inserted straight into the syringe barrel to plug the barrel. Next, water colored by methylene blue was charged into the syringe through the nozzle to a graduation line corresponding to ¾ of the nominal capacity. After the nozzle cap and the plunger were attached, the syringe barrel was placed facing down, and a pressure of 392 kPa was applied to the plunger for 10 seconds. The evaluation was performed for n=20. Then, the syringe was observed under a microscope at a magnification of 10× for the presence of leakage into the valley portion (between the front circular rib and the rear circular rib) of the gasket.

Good: No leakage was observed.
Fair: Slight linear leakage was observed.
Poor: Leakage was clearly observed.

TABLE 1

|  |  | Example No. | | | | | |
| --- | --- | --- | --- | --- | --- | --- | --- |
|  |  | Comparative Example 1 | Example 1 | Example 2 | Example 3 | Example 4 | Example 5 |
| Gasket shape | R1 (mm) | 0.5 | 0.5 | 1.2 | 0.5 | 0.5 | 0.5 |
|  | R2/R1 | 0.8 | 1.2 | 1.2 | 2.0 | 3.5 | 5.0 |
|  | H1 (mm) | 2.8 | 2.8 | 2.8 | 2.8 | 2.8 | 2.8 |
|  | H2/H1 | 3.0 | 3.0 | 3.0 | 3.0 | 3.0 | 3.0 |
|  | H3 (mm) | 6.3 | 6.3 | 6.3 | 6.3 | 6.3 | 6.3 |
|  | H4/H3 | 1.05 | 1.05 | 1.05 | 1.05 | 1.05 | 1.05 |
| Functional test | Sliding resistance (N) | Poor 13 to 18 | Good 9 to 11 | Good 11 to 14 | Good 10 to 12 | Good 10 to 13 | Good 12 to 15 |
|  | Liquid leakage Good | 20/20 | 20/20 | 13/20 | 20/20 | 20/20 | 15/20 |
|  | Fair | 0/20 | 0/20 | 5/20 | 0/20 | 0/20 | 5/20 |
|  | Poor | 0/20 | 0/20 | 2/20 | 0/20 | 0/20 | 0/20 |

In the gasket of Comparative Example 1 in which the radius of curvature R1 of the front corner of the front circular rib is larger than the radius of curvature R2 of the rear corner of the front circular rib, the sliding portion of the gasket makes a strong contact with the barrel and thus shows increased sliding resistance. In contrast, in the gasket of the present invention in which the radius of curvature R1 of the front corner of the front circular rib is smaller than the radius of curvature R2 of the rear corner of the front circular rib, an increase in sliding resistance is prevented while maintaining the contact between the gasket sliding portion and the barrel to an extent that prevents liquid leakage.

REFERENCE SIGNS LIST 1 front circular rib
2 rear circular rib
3 valley portion
R1 radius of curvature of front corner of front circular rib
R2 radius of curvature of rear corner of front circular rib
H1 length of linear portion of front circular rib
H2 length of sliding portion including corner
H3 inner diameter of syringe barrel
H4 diameter of sliding portion of gasket

The invention claimed is:
1. A gasket for prefilled syringes,
the gasket comprising a plurality of circular ribs that are to be in sliding contact with an inner wall of a syringe,
the gasket being laminated with an inert film,
the plurality of circular ribs including a front circular rib having a front corner with a radius of curvature R1 and a rear corner with a radius of curvature R2, and a ratio of the radius of curvature R2 to the radius of curvature R1 being more than 1,
wherein R2 is 0.5 to 3.5 mm.

2. The gasket for prefilled syringes according to claim 1, wherein the ratio of R2 to R1 is 1.2 to 4.

3. The gasket for prefilled syringes according to claim 2, wherein R1 is 0.3 to 1.0 mm.

4. The gasket for prefilled syringes according to claim 3, wherein, provided that a sliding portion of the gasket, including the corner, has a length H2, and a linear portion of the front circular rib has a length H1, a ratio of the length H2 to the length H1 is 2 to 5.

5. The gasket for prefilled syringes according to claim 4, wherein, provided that a sliding portion of the gasket has a diameter H4, and a barrel of the syringe into which the gasket is to be inserted has an inner diameter H3, a ratio of the diameter H4 to the inner diameter H3 is 1.01 to 1.10.

6. The gasket for prefilled syringes according to claim 5, wherein the inert film is a fluororesin film, a nylon resin film, or an olefinic resin film.

7. The gasket for prefilled syringes according to claim 4, wherein the inert film is a fluororesin film, a nylon resin film, or an olefinic resin film.

8. The gasket for prefilled syringes according to claim 3, wherein, provided that a sliding portion of the gasket has a diameter H4, and a barrel of the syringe into which the gasket is to be inserted has an inner diameter H3, a ratio of the diameter H4 to the inner diameter H3 is 1.01 to 1.10.

9. The gasket for prefilled syringes according to claim 3, wherein the inert film is a fluororesin film, a nylon resin film, or an olefinic resin film.

10. The gasket for prefilled syringes according to claim 2, wherein the inert film is a fluororesin film, a nylon resin film, or an olefinic resin film.

11. The gasket for prefilled syringes according to claim 1, wherein R1 is 0.3 to 1.0 mm.

12. The gasket for prefilled syringes according to claim 1, wherein, provided that a sliding portion of the gasket, including the corner, has a length H2, and a linear portion of the front circular rib has a length H1, a ratio of the length H2 to the length H1 is 2 to 5.

13. The gasket for prefilled syringes according to claim 1, wherein, provided that a sliding portion of the gasket has a diameter H4, and a barrel of the syringe into which the gasket is to be inserted has an inner diameter H3, a ratio of the diameter H4 to the inner diameter H3 is 1.01 to 1.10.

14. The gasket for prefilled syringes according to claim 1, wherein the inert film is a fluororesin film, a nylon resin film, or an olefinic resin film.

* * * * *